US012667449B2

(12) United States Patent     (10) Patent No.:   US 12,667,449 B2
Sfeir et al.     (45) Date of Patent:    Jun. 30, 2026

(54) DEGRADABLE MAGNESIUM TENTING DEVICE FOR FASTER SURGERIES AND IMPROVED OUTCOMES IN VERTICAL RIDGE AUGMENTATION

(71) Applicant: UNIVERSITY OF PITTSBURGH-OF THE COMMONWEALTH SYSTEM OF HIGHER EDUCATION, Pittsburgh, PA (US)

(72) Inventors: Charles S. Sfeir, Wexford, PA (US); Andrew J. Brown, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 254 days.

(21) Appl. No.: 17/908,991

(22) PCT Filed: Mar. 16, 2021

(86) PCT No.: PCT/US2021/022508
§ 371 (c)(1),
(2) Date: Sep. 2, 2022

(87) PCT Pub. No.: WO2021/188502
PCT Pub. Date: Sep. 23, 2021

(65) Prior Publication Data
US 2023/0094767 A1    Mar. 30, 2023

Related U.S. Application Data

(60) Provisional application No. 62/990,014, filed on Mar. 16, 2020.

(51) Int. Cl.
*A61C 8/00*      (2006.01)
*A61C 19/06*     (2006.01)
(Continued)

(52) U.S. Cl.
CPC ............ *A61C 8/0012* (2013.01); *A61C 8/008* (2013.01); *A61C 19/063* (2013.01); *A61L 31/128* (2013.01); *A61L 31/148* (2013.01)

(58) Field of Classification Search
CPC .... A61C 8/0012; A61L 31/128; A61L 31/148
See application file for complete search history.

(56) References Cited

U.S. PATENT DOCUMENTS

| | | | |
|---|---|---|---|
| 4,351,069 A | 9/1982 | Ballintyn et al. | |
| 2008/0175885 A1* | 7/2008 | Asgari ................... | B29C 67/04 |
| | | | 424/426 |

(Continued)

FOREIGN PATENT DOCUMENTS

| | | |
|---|---|---|
| CN | 104552621 A | 6/2016 |
| WO | 2015026256 A1 | 2/2015 |

OTHER PUBLICATIONS

Science Direct (source for scientific, technical, and medical research) [online]. [Retrieve Sep. 23, 2024]. Retrieve from the internet: https://www.sciencedirect.com/science/article/pii/S0278239109005564 (Year: 2010).*

(Continued)

*Primary Examiner* — Eric J Rosen
*Assistant Examiner* — Luis Ruiz Martin
(74) *Attorney, Agent, or Firm* — Carol A. Marmo; Eckert Seamans Cherin & Mellott, LLC

(57) ABSTRACT

The invention relates to magnesium screws and screw-like devices for dental implant surgery and, more particularly, to magnesium and magnesium-based tenting devices for implementation in periosteal and gingival tissue overlying an alveolar ridge of a mandible or maxilla to provide vertical ridge augmentation, i.e., bone regeneration. The tenting devices may be composed of magnesium in dry form, such as metallic magnesium and salts thereof; or magnesium alloy including magnesium in dry form and at least one (Continued)

D alloying element or compound; or magnesium-polymer composite including magnesium in dry form and at least one polymer.

18 Claims, 4 Drawing Sheets

(51) Int. Cl.
*A61L 31/12* (2006.01)
*A61L 31/14* (2006.01)

(56) References Cited

U.S. PATENT DOCUMENTS

| | | |
|---|---|---|
| 2010/0023064 A1 | 1/2010 | Brunger et al. |
| 2010/0159418 A1* | 6/2010 | Hall .................... A61C 8/0022 |
| | | 433/201.1 |
| 2017/0014548 A1* | 1/2017 | Sfeir ...................... A61L 27/54 |

OTHER PUBLICATIONS

International Search Report and Written Opinion Issued in International Application No. PCT/US2021/022508 Mailed Jun. 25, 2021.
Brown, Development and Characterization of a Magnesium/Polymer Composite for Guided Bone Regeneration, Doctoral Dissertation, University of Pittsburgh (Jun. 17, 2017).

\* cited by examiner

Magnesium
Titanium
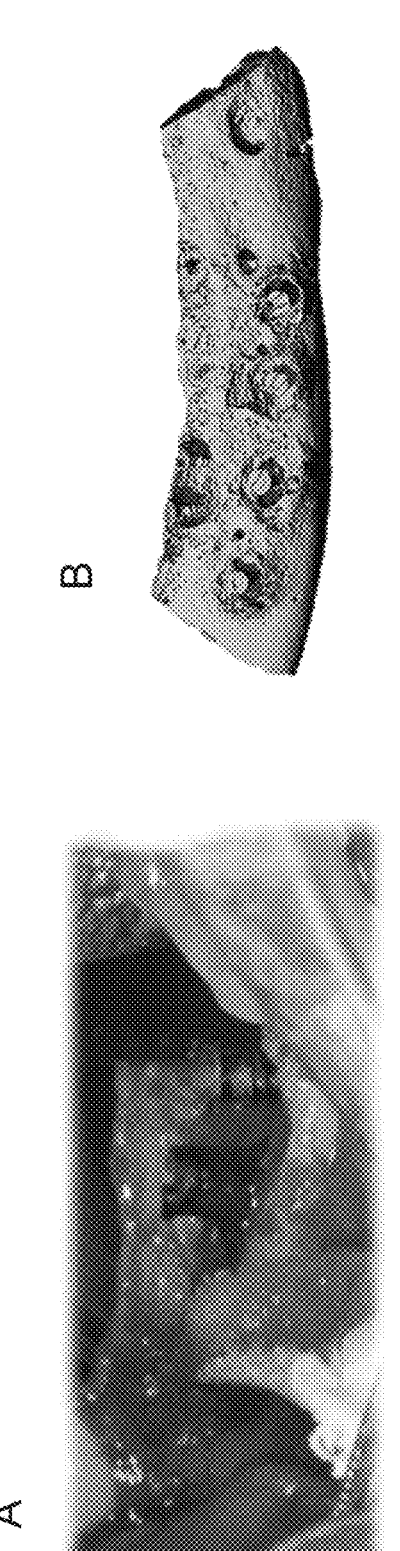
FIGS. 2A, 2B, 2C and 2D

DEGRADABLE MAGNESIUM TENTING DEVICE FOR FASTER SURGERIES AND IMPROVED OUTCOMES IN VERTICAL RIDGE AUGMENTATION

CROSS-REFERENCE TO RELATED APPLICATIONS

This application is a U.S. National Stage Application under 35 U.S.C. § 371 of International Patent Application No. PCT/US2021/022508, filed on Mar. 16, 2021, entitled "DEGRADABLE MAGNESIUM TENTING DEVICE FOR FASTER SURGERIES AND IMPROVED OUT-COMES IN VERTICAL RIDGE AUGMENTATION", which claims priority under 35 U.S.C. § 119 (e) from U.S. provisional patent application No. 62/990,014, entitled "DEGRADABLE MAGNESIUM TENTING DEVICE FOR FASTER SURGERIES AND IMPROVED OUT-COMES IN VERTICAL RIDGE AUGMENTATION" and filed on Mar. 16, 2020, the contents of which are incorporated herein by reference.

FIELD OF THE INVENTION

The invention generally relates to magnesium screws and screw-like devices for dental implant surgery and, more particularly, to magnesium and magnesium-based tenting devices for implementation in periosteal and gingival tissue overlying an alveolar ridge of a mandible or maxilla to provide vertical or horizontal ridge augmentation, i.e., bone regeneration.

BACKGROUND OF THE INVENTION

It is estimated that nearly four million dental bone graft-ing procedures are globally performed every year, and there is a $790 million market for the regenerative materials used in these procedures. Dental bone grafting procedures are most commonly performed in advance of dental implant placement to increase the volume of bone available, in order to properly place the dental implant. An appropriate bony support is essential for proper dental implant placement. The loss of teeth to trauma or disease often results in complex horizontal and vertical alveolar ridge defects, which demand advanced bone augmentation techniques and materials for reconstruction. In North America, approximately 35% of dental bone grafting procedures is performed for vertical ridge augmentation, which has a primary goal to increase the height of the alveolar ridge. Typically, the height of the alveolar ridge is increased by about 3-6 mm.

Various vertical ridge augmentation procedures are known in the art. There are certain known procedures that involve the use of tenting screws. When vertical ridge augmentation is attempted with tenting screws, the follow-ing procedures are typically performed, (i) Guided bone regeneration that refers to a bone graft substitute, which is typically human cadaveric or ani-mal-derived bone particulate, placed into an area where bone regeneration is desired. A barrier membrane is then placed around the bone graft substitute to protect the healing site from mechanical insults and prevent ingrowth of fast-growing gingival tissue into the regen-eration site.

(ii) Periosteal tenting that refers to titanium screws inserted into the alveolar bone as a means of protecting the grafting site from mechanical insult. Frequently, this procedure also uses a bone graft substitute and barrier membrane, as aforementioned for the guided bone regeneration procedure.

Disadvantages associated with guided bone regeneration include one or more of the following: (i) cost of the materials needed, i.e., bone graft substitute and barrier membrane; (ii) time involved for grafting; (iii) need to remove form-stable barrier membranes in a separate procedure; (iv) irritation of gingival tissue and grafting site exposure, and (v) unpre-dictable outcomes, e.g., approximately 25 percent of first vertical ridge augmentation procedures require performance of a later second graft to achieve optimal outcomes. Since periosteal tenting frequently uses a bone graft substitute and barrier membrane, the disadvantages associated with guided bone regeneration are also associated with periosteal tenting. In addition, there are drawbacks in the periosteal tenting procedures due to the use of titanium, i.e., non-biodegrad-able, screws.

Many implant devices are traditionally constructed of metal. These materials of construction exhibit good biome-chanical properties. Traditional metallic biomaterials, such as, titanium and stainless steel, in particular, have appropri-ate properties such as high strength, ductility, fracture tough-ness, hardness, corrosion resistance, formability, and bio-compatibility to make them attractive for most load-bearing applications. However, many traditional metallic biomate-rials used for implant devices are not biodegradable. The stiffness and other material properties of traditional metallic biomaterials can also cause irritation of overlying gingival tissue which affects bone regeneration reliability and aes-thetic outcomes. Therefore, there is a desire in the biomedi-cal field to develop biodegradable materials for implant devices. Polymers, such as polyhydroxy acids, polylactic acid (PLA), polyglycolic acid (PGA), and the like are known as conventional biodegradable biomaterials. However, in some instances, the strength and ductility exhibited by polymers are not as attractive as those demonstrated by metallic biomaterials. In addition, in some instances, the polymer produces acidic degradation by-products, which negatively affects protein and drug bioavailability in drug delivery applications.

Thus, there is a desire and need in the biomedical field to develop biodegradable materials for implant devices that demonstrate an acceptable level of strength, ductility and osteoconductivity. For example, magnesium is attractive as a biomaterial because it is very lightweight, has a density similar to cortical bone, has an elastic modulus close to natural bone, is essential to human metabolism, is a cofactor for many enzymes, stabilizes the structures of DNA and RNA, and degrades safely in the body.

There is an additional consideration when designing bio-degradable medical devices compared to non-degradable medical devices. As the devices degrades there is a loss in functionality. Simply mirroring the design of a non-degrad-able device (e.g. titanium tenting screw) onto a biodegrad-able material (e.g. magnesium) will not necessarily impart the device performance required to meet user needs.

Medical implant devices constructed of biodegradable biomaterials provide the capability for the devices to degrade over a period of time, e.g., by dissolving in the physiological environment, such that surgery is not required for removal when the implant devices are no longer needed.

In the field of biomedical applications, there is a desire to develop biocompatible materials of construction for medical implant devices that are effective for bone regeneration and drug delivery. In accordance with the invention, there is a desire to develop magnesium and magnesium-containing materials, e.g., magnesium-based alloys and magnesium-polymer composites, for medical implant construction which emphasize beneficial properties of magnesium, such as osteoconductive properties, and also de-emphasize detrimental properties of polymer, such as acidic by-products due to degradation.

Thus, it would be advantageous to develop screws or screw-like devices for dental implant surgery composed of a biodegradable material, such that a separate procedure for their subsequent removal may be precluded. More particularly, there is a need in the art to develop magnesium and magnesium-containing tenting devices for implementation in periosteal and gingival tissue overlying an alveolar ridge of a mandible or maxilla to provide vertical ridge augmentation, i.e., bone regeneration. Further benefits could be derived from obviating the need for the bone graft substitute and barrier membrane.

BRIEF DESCRIPTION OF THE DRAWINGS

A full understanding of the disclosed concept can be gained from the following description of the preferred embodiments when read in conjunction with the accompanying drawings.

FIGS. 2A-2D are images that show magnesium (99.9% pure magnesium) and titanium (control) tenting screws implanted in a partially edentulous canine alveolar ridge, wherein FIGS. 2A and 2B show the magnesium tenting screws at the time of implantation and subsequent bone regeneration that occurred over eight weeks after implantation, respectively, and FIGS. 2C and 2D show the titanium tenting screws at the time of implantation and eight weeks later that did not result in bone regeneration, respectively, in accordance with certain embodiments of the invention;

DETAILED DESCRIPTION OF THE INVENTION

Figure 1A:
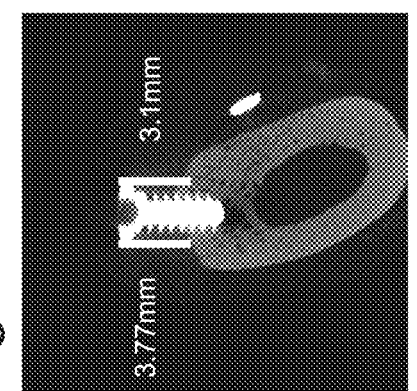
FIG. 1A shows the insertion of titanium (i.e. traditional) tenting screws in a partially edentulous canine alveolar ridge to encourage vertical ridge augmentation. An experiment was conducted wherein titanium and magnesium screws of similar size were inserted at identical heights in the alveolar ridge and covered with barrier membranes to elicit vertical ridge augmentation.

The invention relates to systems and methods for vertical or horizontal ridge augmentation, and tenting devices utilized in dental surgical procedures to provide improved bone regeneration. In accordance with the invention, the tenting devices include biodegradable screws or screw-like devices that are implanted in periosteal and gingival tissue overlying an alveolar ridge of a mandible or maxilla to provide vertical or horizontal ridge augmentation, i.e., bone regeneration. The screws or screw-like devices are composed of magnesium or magnesium-based material, such as, metallic or elemental magnesium, magnesium salt, magnesium alloy, or magnesium composite, e.g., magnesium-polymer composite. The screws or screw-like devices are useful to tent the periosteal and gingival tissue overlying the alveolar ridge of the mandible or maxilla. Non-limiting examples of suitable magnesium alloys include a magnesium element or component or salt thereof, and one or more alloying elements or components. Suitable alloying elements or components are selected from those known in the art, such as, but not limited to zinc (Zn), zirconium (Zr), calcium (Ca), yttrium (Y), manganese (Mn), and the like. In certain embodiments, the magnesium alloy includes 1.22 wt. % zinc, 0.43 wt. % Ca and 0.44 wt. % Mn, with the remainder being Mg (and impurities) based on the total weight of the alloy. Non-limiting examples of suitable magnesium composites include a magnesium element or component or salt thereof, and one or more polymer components, such as, calcium phosphate, hydroxyapatite, lecithin, collagen, fibrin, gelatin, silk, elastin, chitosan, starch, alginate, hyaluronic acid, chondroitin, agarose, cellulose, polyester, poly(glycolic acid) (PGA), poly(L-lactic acid) (PLA), poly(lactic-co-glycolic acid) (PLGA), poly(caprolactone) (PCL), poly(propylene fumarate), polyorthoester, polyanhydride, poly(ethylene glycol) (PEG), polycarbonate, polyurethane, elastomer, poly(glycerol sebacate) (PGS), or mixtures thereof. In certain embodiments, the elemental magnesium or salt thereof, or the magnesium component, e.g., for the alloys and composites, is in a dry form, such as powder, particles or grains.

With respect to the magnesium/polymer composite, a concentration of the magnesium component may be selected to effectively buffer acidic by-products of degradation of the polymer component. The purity of the magnesium may be selected to control degradation rate. In certain embodiments, the magnesium component includes from about 99 to about 99.95 weight percent magnesium based on total weight. Conventional polymers for use in constructing medical implants have been found to produce acidic by-products, which can cause inflammation in surrounding tissue and result in jeopardizing drug, gene and protein delivery capabilities of the implants. It has been found that the presence of magnesium in combination with polymer produces a medical implant device that exhibits a degradation profile to buffer polymer-related acidity, and may ultimately improve the in-vivo performance of the medical implant device.

The magnesium or magnesium-based material that composes the screws or screw-like devices for tenting provides for biodegradation of the devices over a period of time. Advantages associated with these magnesium or magnesium-based tenting devices, e.g., as compared to titanium devices, include one or more of the following: (i) less regenerative materials needed, (ii) lower expense of the procedure; (iii) faster bone grafting procedure; (iv) preclusion of separate procedure to remove the device; (v) improved outcome, e.g., increased height of regenerated bone; (vi) increased pace to dental implant placement; and (vii) decreased likelihood of adverse effects to the patient.

The magnesium or magnesium-based tenting devices are effective to provide a sustained release or delivery of magnesium to the periosteal and/or gingival tissue overlying an alveolar ridge of a mandible or maxilla to provide vertical ridge augmentation. The release of magnesium into a bone/tissue environment is effective to permit bone/tissue growth and/or regeneration. Furthermore, metal ions, such as, magnesium ions, contribute to the formation of bone/tissue. With respect to the magnesium/polymer composites, the polymer component is employed as a delivery system for magnesium, e.g., magnesium ions, into the bone/tissue environment. In certain embodiments, the magnesium and magnesium-polymer devices, e.g., tenting screws or screw-like devices, have a porous framework or configuration. The porosity is manufactured using conventional apparatus and processes, such as, pressing, sintering and solvent casting with salt leaching.

Magnesium or a magnesium-based material in a dry form, e.g., powder, particles and grains, is not typically used in the art of 3D-printing primarily due to safety concerns relating to magnesium. However, in accordance with the invention, a composite of dry form magnesium and polymer enables 3D-printing of the implant tenting screws or screw-like devices.

In certain embodiments, at least one active substance is attached to the surface of the tenting device, or encapsulated therein. As used herein, the term "active substance" describes a molecule, compound, complex, adduct and/or composite that exhibits one or more beneficial activities such as therapeutic activity, diagnostic activity, biocompatibility, corrosion, and the like. Active substances that exhibit a therapeutic activity include bioactive agents, pharmaceutically active agents, drugs and the like. Non-limiting examples of bioactive agents include, but are not limited to, bone growth promoting agents such as growth factors, drugs, proteins, antibiotics, antibodies, ligands, DNA, RNA, peptides, enzymes, vitamins, cells and the like, and combinations thereof.

Moreover, as described herein, the magnesium/polymer composites are effective to provide a sustained and controlled release of magnesium to periosteal and gingival tissue overlying the alveolar ridge of a mandible or maxilla to provide vertical ridge augmentation.

In certain embodiments, one or more additional known elements, compounds and additives is/are included with the magnesium component and/or alloy component and/or polymer component, to impart additional/different characteristics and properties, provided that non-toxicity is maintained within acceptable limits. The additional elements, compounds and additives are selected from a wide variety known in the art, such as but not limited to, strontium, manganese, calcium, zinc, rare earth elements, silver, and mixtures and combinations thereof. For example, silver is added to provide anti-microbial properties.

In general, the amount of each of the components or elements in the magnesium tenting screws or screw-like devices varies and the amount is selected such that acceptable non-toxic limits, biocompatibility, and degradability over a period of time are achieved. In certain embodiments, the amount is selected such that the devices exhibit corrosion resistance in the presence of water and body fluids allowing for suitable in vitro use in physiological environments, and exhibit corrosion resistance with minimal or no evolution of hydrogen gas as the evolution of hydrogen, e.g., hydrogen bubbles, is known to cause complications. Acceptable non-toxic limits and time frames for degradation vary, and depend upon the particular physical and physiological characteristics.

The magnesium or magnesium-based screws or screw-like devices for tenting are prepared using various conventional techniques and processes known in the art. The magnesium and alloying elements/components are melted or alloyed at an elevated temperature using conventional methods known in the art. In certain embodiments, high energy mechanical alloying (HEMA), uniaxial or isostatic compaction, and sintering is used.

In general, pressing, sintering and solvent casting with salt leaching methods are employed. It is contemplated that properties and characteristics of the cast device are impacted by use of a particular casting process. The resulting cast is subjected to various forming and finishing processes known in the art. Non-limiting examples of such processes include, but are not limited to, extrusion, forging, polishing (by mechanical and/or chemical means), surface treating (to form a superficial layer on the surface) and combinations thereof. In certain embodiments, a molten alloyed composition is poured into a mold, allowed to cool and thereby solidify.

The HEMA and casting processes are typically conducted under a protective atmosphere to preclude, minimize or reduce decomposition of the components, e.g., especially the magnesium component. The protective atmosphere includes one or more compounds selected from those known in the art, such as but not limited to, argon and sulfur hexafluoride.

Suitable design structures for the bone screws or screw-like devices vary. In general, the tenting screws or screw-like devices include a head having a top surface and a bottom surface, and a shaft attached to the bottom surface of the head and extending perpendicularly therefrom, according to conventional screw designs and geometries. In certain embodiments, the screws include a cylindrical head having a top planar surface and a bottom planar surface, a cylindrical shaft extending perpendicularly from the bottom planar surface wherein the shaft is partially threaded, and a pointed tip.

A degradable tenting device (e.g., magnesium or magnesium alloy tenting screw) according to the invention and a non-degradable tenting device (e.g., titanium tenting screw) that have the same design or geometry can demonstrate different performance characteristics and properties. In certain embodiments, the design or geometry of the degradable tenting device is selected to impart improved or enhanced performance characteristics and/or properties (e.g., similar to the performance of the non-degradable device). In exemplary embodiments, the porosity and/or geometry of the degradable tenting device is modified to provide staged or phased resorption of the tenting device when implanted. The porosity and/or geometry is selected such that a specific portion(s) or component(s) of the tenting device is resorbed in a shorter period of time as compared to another portion(s) or component(s) of the tenting device. For example, the portion(s) or component(s) of the tenting device that is implanted in bone or tissue has a lower porosity as compared to the porosity of the portion(s) or component(s) that is not implanted in the bone or tissue, such that the time period for resorption of the bone- or tissue-implanted portion(s) or component(s) of the tenting device is longer as compared to the time period for resorption of the portion(s) or component(s) of the tenting device that is not implanted in the bone or tissue. The tenting device has different or various porosities to control the rate of resorption for specific portions or components. For example, a screw shaft that is implanted in bone or tissue has a lower porosity than the screw head that is not implanted in the bone or tissue. The screw head is resorbed in a shorter period of time as compared to the screw shaft. In certain embodiments, there are varying porosities throughout the screw head or shaft such that each of the screw head and screw shaft have gradually lower, e.g., a gradient of reducing, porosities and corresponding resorption rates. For example, there is a gradient of decreasing porosity extending along the length of the tenting device from the top surface of the screw head having the highest porosity to the tip or end point of the screw shaft having the lowest porosity. The screw shaft near the tip or end point of the screw is the last portion to be resorbed.

In certain embodiments, the degradable tenting device according to the invention has a design or geometry selected such that portion(s) or component(s) of the tenting device that is implanted in bone or tissue has a lower surface area to volume ratio as compared to the surface area to volume ratio of the portion(s) or component(s) that is not implanted in the bone or tissue, such that the time period for resorption of the bone- or tissue-implanted portion(s) or component(s) of the tenting device is longer as compared to the time period for resorption of the portion(s) or component(s) of the tenting device that is not implanted in the bone or tissue. The tenting device has different or various surface area to volume ratios to control the rate of resorption for specific portions or components. For example, a screw shaft that is implanted in bone or tissue has a geometry that imparts lower surface to volume ratio than the screw head that is not implanted in the bone or tissue. The screw head is resorbed in a shorter period of time as compared to the screw shaft. In certain embodiments, there are different geometries that impart varying surface area to volume ratios throughout the screw head or shaft such that each of the screw head and screw shaft have gradually lower, e.g., a gradient of reducing, surface area to volume ratios and corresponding resorption rates. For example, there is a gradient of decreasing surface area to volume ratios extending along the length of the tenting device from the top surface of the screw head having the highest surface area to volume ratio, to the tip or end point of the screw shaft having the lowest surface area to volume ratio. The screw shaft near the tip or end point of the screw is the last portion to be resorbed.

In certain embodiments, a portion of the tenting device has a resorption rate that is different as compared to another portion of the tenting device. In an exemplary embodiment, the head is resorbed in a shorter time period as compared to the shaft.

In certain embodiments, the head of the tenting device has a higher porosity as compared to the shaft and/or the head has a higher surface to volume ratio as compared to the shaft.

In certain embodiments, the porosity and/or surface area to volume ratio is a decreasing gradient extending along a length of the tenting device from a top surface of the head to an opposite end point or tip of the shaft.

Figure 1B:
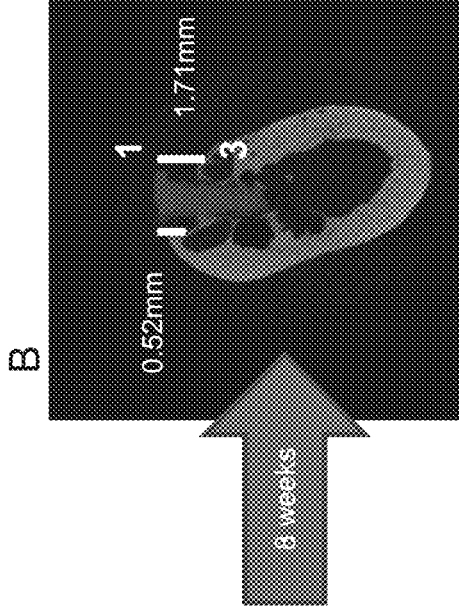
FIG. 1B shows a radiographic image with measurements of vertical ridge augmentation obtained following 8 weeks of healing surrounding a magnesium tenting screw, in accordance with certain embodiments of the invention.
Figure 4:
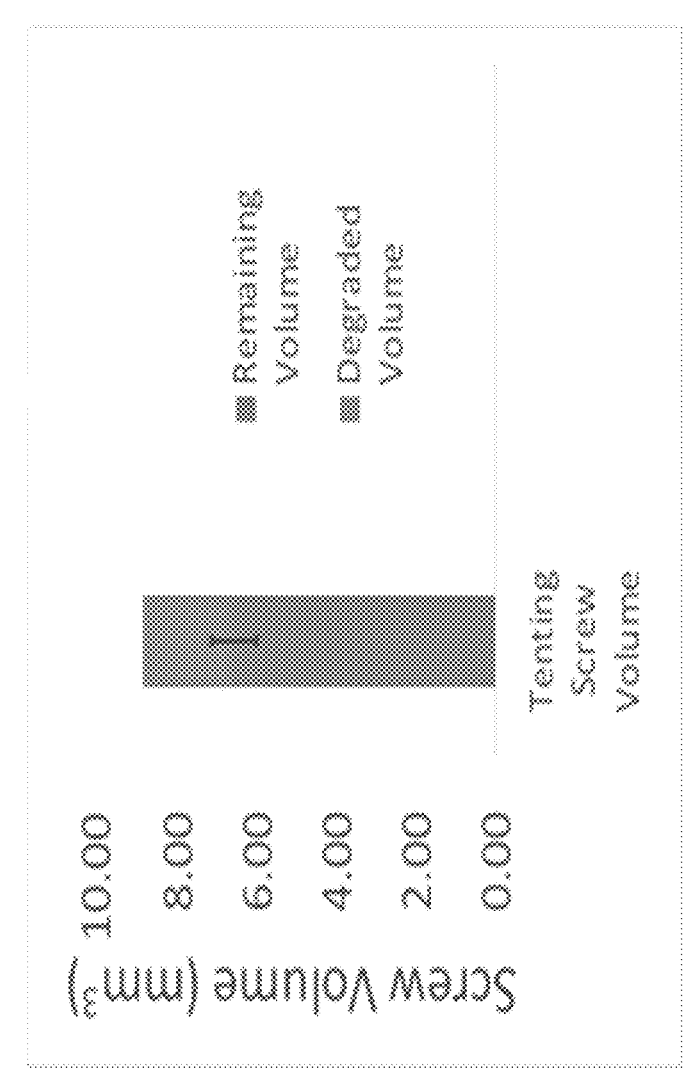
FIG. 4 is a plot that shows screw volume lost (26%) over a period of eight weeks for magnesium tenting screws implanted in periosteal and gingival tissue overlying an alveolar ridge of a mandible or maxilla, in accordance with certain embodiments of the invention.

The use of magnesium or magnesium-based screws or screw-like devices is effective to provide alveolar ridge augmentation because of bone regeneration that occurs, due to the release of magnesium ions in the area surrounding the implanted screws or screw-like devices and biodegradation of the screws or screw-like devices. The inventors have surprisingly found that the screw or screw-like device head ridge depth decreases over a period of time for the magnesium or magnesium-based screws or screw-like devices. The term "head ridge depth" or "screw head ridge depth" as used herein and the claims means the distance or height between the top surface of the head of the screw or screw-like device and the top surface of the alveolar ridge. In certain embodiments, the screw head ridge depth of the magnesium or magnesium-based screws as-implanted in the aveolar ridge is about 3.0 mm, i.e., measured from the top surface of the alveolar ridge to the top surface of the screw head. The image in FIG. 1B shows that after a period of eight weeks implanted, the screw head ridge depth (measured along the white vertical line extending from the screw head top surface 1 to the alveolar ridge top surface 3) of the magnesium tenting screw according to the invention is reduced to about 0.52 mm on one side and about 1.71 mm on another side of the head of the screw. Thus, the difference between the screw head ridge depth at implantation and eight weeks later is due to the bone regeneration that occurs due to the magnesium or magnesium-based composition and construction of the screws or screw-like devices. In addition, during the time period of implantation, e.g., eight weeks, the volume of the magnesium or magnesium-based screw or screw-like device is also reduced due to its biodegradation. The plot in FIG. 4 shows that a magnesium or magnesium-based screw or screw-like device as-implanted has a volume of about 8.8 $mm^3$, whereas the volume after eight weeks of implantation is about 6.6 $mm^3$. In comparison, a titanium screw implanted for eight weeks does not biodegrade and therefore, the volume after eight weeks of implantation is the same as the volume of the titanium screw as implanted.

Figure 3:
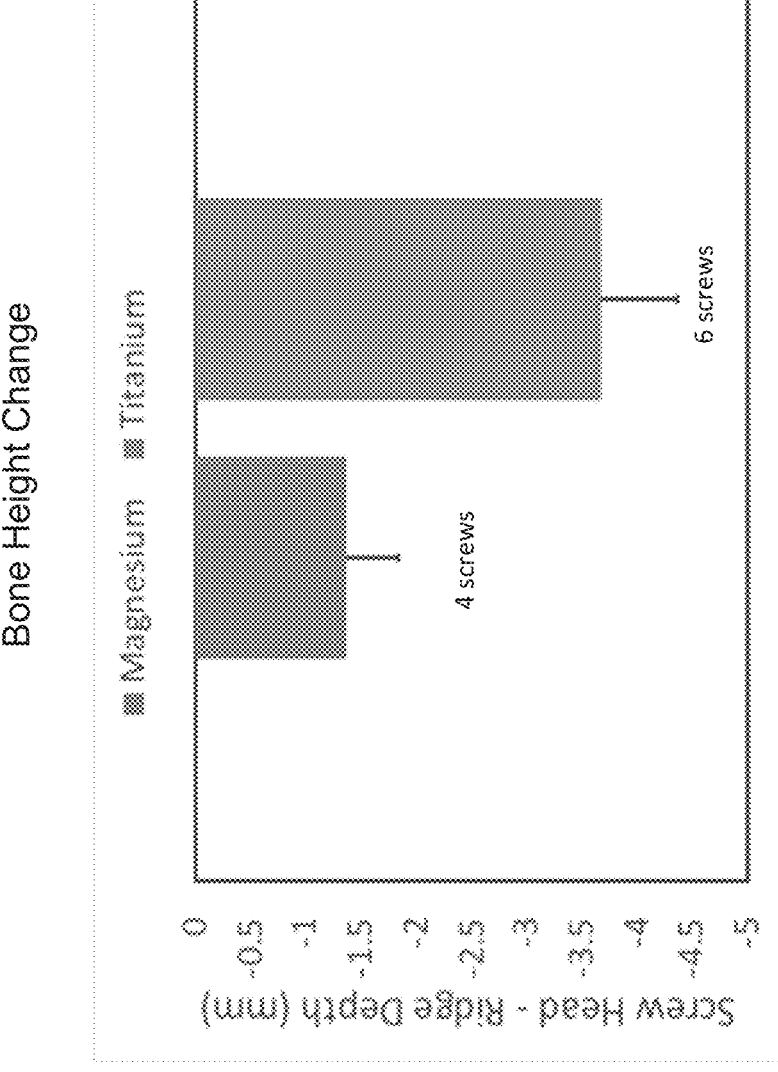
FIG. 3 is a plot that shows the change in bone height for four magnesium tenting screws and six titanium (control) tenting screws from the time of implantation to ex-plantation, whereby the remaining defect height was only 1.3 mm for the magnesium tenting screws and 3.6 mm for the titanium tenting screws, in accordance with certain embodiments of the invention.

The magnesium and magnesium-based medical implant devices, e.g., tenting screws or screw-like devices, when implanted in periosteal and gingival tissue overlaying an alveolar ridge of a mandible or maxilla are effective to regenerate bone such as to provide vertical ridge augmentation, e.g., an increase in the vertical height of the alveolar ridge. In certain embodiments, the amount or level of bone regeneration or vertical ridge augmentation is determined by measuring the screw head ridge depth at the time of implantation and at a period of time thereafter, as above-described. As aforementioned, the difference in screw head ridge depth from the time of implantation of the screw in the periosteal or gingival tissue to eight weeks later, is from about 3.0 mm at implantation to about 1.71 mm to 0.52 mm at eight weeks (as shown in FIG. 1B). This results in a difference in the range of approximately 1.3 mm to 2.5 mm, which corresponds to an increase in the vertical height of the alveolar ridge in the range of 1.3 mm to 2.5 mm (as shown in FIG. 3). In certain other embodiments, as shown in FIG. 4, the tenting screws degrade by about 26% over an eight week period and, in some instances, bone regenerates above or over the top surface of the head for the magnesium tenting screws. The magnesium and magnesium-based tenting screws according to the invention are effective to grow bone growth above and around the screws where there previously was no bone.

EXAMPLES

Figure 1C:
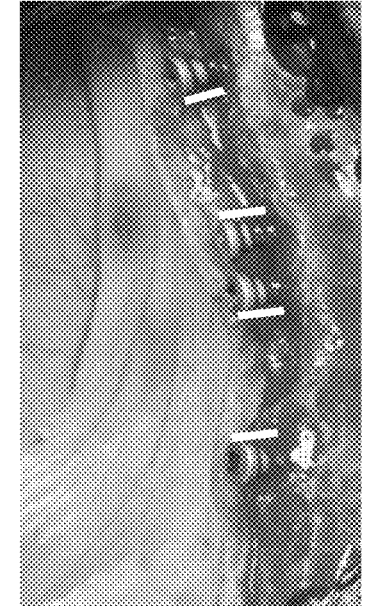
FIG. 1C shows a radiographic image with measurements of vertical ridge augmentation obtained following 8 weeks of healing surrounding a titanium tenting screw. There was increased vertical ridge augmentation obtained surrounding the magnesium tenting screws in FIG. 1B.

Titanium and magnesium screw devices of similar size were inserted at identical heights in an alveolar ridge to elicit vertical ridge augmentation. FIG. 1A shows the titanium (i.e. traditional) tenting screws in a partially edentulous canine alveolar ridge. The magnesium (99.9% magnesium) tenting screw device was implanted in vivo into canine saddle defects and regeneration was permitted to occur for a period of 8 weeks. FIG. 1B shows a radiographic image with measurements of vertical ridge augmentation obtained following 8 weeks of healing surrounding the magnesium tenting screw. FIG. 1C shows a radiographic image with measurements of vertical ridge augmentation obtained following 8 weeks of healing surrounding a titanium tenting screw. There was increased vertical ridge augmentation obtained surrounding the magnesium tenting screw in FIG. 1B. FIGS. 2A-2D are images that show the magnesium (99.9% pure magnesium) and titanium (control) tenting screws implanted in the alveolar ridge, wherein FIGS. 2A and 2B show the magnesium tenting screws at the time of implantation and subsequent bone regeneration that occurred over eight weeks after implantation, respectively, and FIGS. 2C and 2D show the titanium tenting screws at the time of implantation and eight weeks later that did not result in bone regeneration, respectively. As shown in FIGS. 2A and 2B, no adverse events were observed during the 8-week healing phase for the magnesium tenting screws, unlike the titanium control devices shown in FIGS. 2C and 2D. Upon ex-plantation of the tenting screw device, it was found that the remaining defect height for the magnesium tenting screws was only 1.3 mm as compared to 3.6 mm for the control titanium tenting screws (as shown in FIG. 3). Further, good bone-device contact was identified for the magnesium tenting screws, which suggested good osteointegration and biocompatibility. The tenting screws degraded 26% over the 8 week healing period (as shown in FIG. 4). In some instances, it was found that bone regenerated above the top surface of the head for the magnesium tenting screws.

In an additional in vivo procedure, wherein magnesium tenting screws were implanted into a canine alveolar ridge with no defect created, four surgical sites received magnesium tenting screws and four surgical sites received titanium tenting screws. Alveolar ridge samples were explanted at either 8-week or sixteen week periods after surgeries, and subjected to microCT analysis. It was found that bone growth was present above and around all the magnesium screws where there previously was no bone. However, no bone growth was present around the control titanium screws.

Thus, the magnesium or magnesium-based alloy tenting screw devices according to the invention provide a reliable, e.g., more reliable than prior art titanium tenting screws, technique to obtain regeneration of the alveolar ridge in the vertical component.

Since, after bone healing is complete, the implant devices are no longer needed, the titanium devices are left in situ or, alternatively, removed by performing a separate procedure. Whereas, the magnesium or magnesium-based alloy devices of the invention degrade over a period of time and therefore, they will not be left in situ and a removal procedure is not required. Biodegradation of the devices is preferred because leaving the screws in situ increases the chances of infection and rejection, and their removal requires a second surgery and causes a risk of infection, pain and discomfort to the patient, as well as an additional expense. Moreover, magnesium and magnesium-based alloys are suitable materials for the construction of grafting devices because they have mechanical properties compatible to bone and can be resorbed over a period of time.

It should be understood that the embodiments described herein and the examples above are for illustrative purposes only and that various modifications or changes in light thereof will be suggested to persons skilled in the art and are to be included within the spirit and purview of this application.

The invention claimed is:

1. A dental tenting device, comprising:
   at least one biodegradable screw device, comprising:
   a composition, comprising:
   magnesium in dry form; or
   a magnesium-based alloy, comprising:
   magnesium in dry form; and
   at least one alloying element or compound; or a magnesium-polymer composite, comprising:
   magnesium in dry form; and
   at least one polymer; and
a porous device framework, comprising:
   a screw head comprising a top surface and a bottom surface, wherein the screw head has a first porosity and a first resorption rate;
   a screw shaft connected to the bottom surface of the screw head extending perpendicularly therefrom to an end of the screw shaft,
wherein the screw shaft has a second porosity that is less than the first porosity and a second resorption rate that is lower than the first resorption rate,
wherein the screw head extending from the top surface to the bottom surface is resorbed in a shorter time than the screw shaft extending from the bottom surface of the screw head to the end of the screw shaft,
wherein the screw device is configured to be implanted in periosteal and/or gingival tissue overlying an alveolar ridge of a mandible or maxilla, and
wherein a sustained release of magnesium ions from the screw device to the periosteal and/or gingival tissue is effective to heal and/or regenerate tissue to increase a vertical height of the alveolar ridge.

2. The dental tenting device of claim 1, wherein the magnesium in dry form is selected from the group consisting of particles, grains and powder of metallic magnesium, magnesium salt, and combinations and blends thereof.

3. The dental tenting device of claim 1, wherein the at least one polymer is selected from the group consisting of calcium phosphate, hydroxyapatite, lecithin, collagen, fibrin, gelatin, silk, elastin, chitosan, starch, alginate, hyaluronic acid, chondroitin, agarose, cellulose, polyester, poly(glycolic acid), poly(L-lactic acid), poly(lactic-co-glycolic acid), poly(caprolactone), poly(propylene fumarate), polyorthoester, polyanhydride, poly(ethylene glycol), polycarbonate, polyurethane, elastomer, poly(glycerol sebacate), and mixtures thereof.

4. The dental tenting device of claim 1, wherein concentration of the magnesium in dry form for the magnesium-polymer composite is selected such that said concentration is effective to buffer acidic by-products of degradation of the polymer.

5. The dental tenting device of claim 1, wherein the magnesium in dry form comprises from about 99 to about 99.95 weight percent magnesium based on total weight.

6. The dental tenting device of claim 1, wherein the tissue is bone.

7. The dental tenting device of claim 1, wherein a plurality of pores are formed in the screw device.

8. The dental tenting device of claim 7, wherein the plurality of pores are employed for drug delivery.

9. The dental tenting device of claim 1, wherein the screw head has a higher surface to volume ratio as compared to the screw shaft.

10. The dental tenting device of claim 1, wherein the first resorption rate comprises a decreasing gradient extending along a length of the screw head from the top surface to the bottom surface, and the second resorption rate comprises a decreasing gradient extending along a length of the screw shaft from the bottom surface of the screw head to an opposite end point of the screw shaft.

11. The dental tenting device of claim 1, wherein the first porosity comprises a decreasing gradient extending along a length of the screw head from the top surface to the bottom surface, and the second porosity comprises a decreasing gradient extending along a length of the screw shaft from the bottom surface of the screw head to an opposite end point of the screw shaft.

12. A method of making a tenting device, comprising:

preparing a porous device framework, comprising:

preparing a magnesium, magnesium alloy or magnesium-polymer composite, comprising:

(a) selecting magnesium in dry form; or (b) selecting magnesium in dry form; and combining the magnesium with at least one alloying element or compound to produce the magnesium alloy; or (c) selecting magnesium in dry form; and (d) combining with at least one polymer to form the magnesium-polymer composite;

forming a screw device from the magnesium, magnesium alloy or magnesium-polymer composite, comprising:

a screw head comprising a top surface and a bottom surface, wherein the screw head has a first porosity and a first resorption rate;

a screw shaft connected to the bottom surface of the screw head and extending perpendicularly therefrom to an end of the screw shaft, wherein the screw shaft has a second porosity that is less than the first porosity and a second resorption rate that is lower than the first resorption rate, wherein the screw head extending from the top surface to the bottom surface is resorbed in a shorter time than the screw shaft extending from the bottom surface of the screw head to the end of the screw shaft, wherein the screw device is configured to be implanted in a periosteal and/or gingival tissue overlying an alveolar ridge of a mandible or maxilla, to provide a sustained release of magnesium ions from the screw device to the periosteal and/or gingival tissue to effectively heal and/or regenerate tissue to increase a vertical height of the alveolar ridge.

13. The dental tenting device of claim 1, further comprising:

a screw tip connected to a distal end of the screw shaft, wherein the screw tip has a different third resorption rate that is lower than the first resorption rate of the screw head and lower than the second resorption rate of the screw shaft, and a different third porosity that is less than the first porosity of the screw head and less than the second porosity of the screw shaft.

14. The method of claim 12, wherein the first porosity comprises a decreasing gradient extending along a length of the screw head from the top surface to the bottom surface, and the second porosity comprises a decreasing gradient extending along a length of the screw shaft from the bottom surface of the screw head to an opposite end point of the screw shaft.

15. The method of claim 12, further comprising:

forming a screw tip connected to a distal end of the screw shaft, wherein the screw tip has a different third resorption rate that is lower than the first resorption rate of the screw head and lower than the second resorption rate of the screw shaft, and a different third porosity that is less than the first porosity of the screw head and less than the second porosity of the screw shaft.

16. The method of claim 12, wherein the first resorption rate comprises a decreasing gradient extending along a length of the screw head from the top surface to the bottom surface, and the second resorption rate comprises a decreasing gradient extending along a length of the screw shaft from the bottom surface of the screw head to an opposite end point of the screw shaft.

17. The dental tenting device of claim 1, wherein there is a gradient of decreasing porosity extending along a length of the tenting device from the top surface of the screw head having the highest porosity to the end surface of the screw shaft having the lowest porosity.

18. The method of claim 12, wherein there is a gradient of decreasing porosity extending along a length of the tenting device from the top surface of the screw head having the highest porosity to the end surface of the screw shaft having the lowest porosity.

* * * * *